(12) United States Patent  
Sherman et al.

(10) Patent No.: US 8,974,436 B2
(45) Date of Patent: Mar. 10, 2015

(54) MULTI-SECTIONED CANNULA WITH MULTIPLE LUMENS

(75) Inventors: Ethan G. Sherman, Jacksonville, FL (US); David J. Little, Ponte Vedra, FL (US); Wei Chen, St. Johns, FL (US); John R. Prisco, Jacksonville, FL (US); Matthew J. Friend, St. Augustine, FL (US); Matthew F. Myntti, St. Augustine, FL (US); Tom Zelmer, Raleigh, NC (US); Cyan Godfrey, Chapel Hill, NC (US); Roy Attride, Raleigh, NC (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/284,387

(22) Filed: Oct. 28, 2011

(65) Prior Publication Data

US 2013/0110157 A1    May 2, 2013

(51) Int. Cl.
*A61M 25/00* (2006.01)
*A61M 31/00* (2006.01)
*A61M 3/02* (2006.01)
*A61M 11/00* (2006.01)
*A61B 17/00* (2006.01)
*A61M 15/00* (2006.01)
*A61M 37/00* (2006.01)
*A61M 11/02* (2006.01)
*A61M 15/08* (2006.01)

(52) U.S. Cl.
CPC ........... *A61M 25/008* (2013.01); *A61M 3/0279* (2013.01); *A61M 11/00* (2013.01); *A61B 17/00491* (2013.01); *A61M 11/007* (2013.01); *A61M 15/0003* (2013.01); *A61M 25/0071* (2013.01); *A61M 2210/0618* (2013.01); *A61M 2210/0681* (2013.01); *A61B 2017/00495* (2013.01); *A61M 11/02* (2013.01); *A61M 15/08* (2013.01)
USPC ........................... 604/525; 604/82; 604/93.01

(58) Field of Classification Search
USPC .................................. 604/523–527, 533–535
See application file for complete search history.

(56) References Cited

U.S. PATENT DOCUMENTS

| 1,906,991 | A  | 5/1933  | McTernan     |
|-----------|----|---------|--------------|
| 4,700,894 | A  | 10/1987 | Grzych       |
| 5,464,396 | A  | 11/1995 | Barta et al. |
| 5,788,667 | A  | 8/1998  | Stoller      |
| 6,112,743 | A  | 9/2000  | Denton       |
| 6,319,248 | B1 | 11/2001 | Nahon        |

(Continued)

FOREIGN PATENT DOCUMENTS

| DE | 3108918 A1 | 9/1982 |
| EP | 0363519 A1 | 4/1990 |

(Continued)

OTHER PUBLICATIONS

Wolfe Tory Medical, Inc. Brochure, "It's MADgic Laryngo-Tracheal Mucosal Atomization Device", printed Apr. 27, 2011 from the Internet.

*Primary Examiner* — Nathan R Price
(74) *Attorney, Agent, or Firm* — IPLM Group, P.A.

(57) ABSTRACT

A malleable cannula having multiple lumens, constrained at the proximal end portion to provide rigidity and malleable at the distal end portion. The cannula has a combination of flexibility and stiffness that assists in accessing body passageways without kinking.

28 Claims, 5 Drawing Sheets

(56) References Cited

U.S. PATENT DOCUMENTS

| | | |
|---|---|---|
| 6,926,711 B2 | 8/2005 | Lentz et al. |
| 6,936,033 B2 | 8/2005 | McIntosh et al. |
| 6,976,979 B2 * | 12/2005 | Lawrence et al. .............. 604/524 |
| 7,455,248 B2 | 11/2008 | Kablik et al. |
| 7,635,343 B2 | 12/2009 | McIntosh et al. |
| 7,637,901 B2 * | 12/2009 | Lawrence et al. .............. 604/524 |
| 2001/0001812 A1 * | 5/2001 | Valley et al. ................ 604/96.01 |
| 2001/0016702 A1 * | 8/2001 | Benjamin ........................ 604/19 |
| 2002/0177840 A1 * | 11/2002 | Farnholtz ....................... 604/523 |
| 2003/0018318 A1 * | 1/2003 | Melsky .......................... 604/526 |
| 2003/0135198 A1 * | 7/2003 | Berhow et al. ................. 604/524 |
| 2004/0059283 A1 | 3/2004 | Kirwan et al. |
| 2004/0087885 A1 * | 5/2004 | Kawano et al. .................... 604/8 |
| 2004/0087932 A1 * | 5/2004 | Lawrence et al. .............. 604/524 |
| 2005/0119609 A1 | 6/2005 | McLean |
| 2006/0020256 A1 * | 1/2006 | Bell et al. ....................... 604/523 |
| 2006/0253082 A1 | 11/2006 | McIntosh et al. |
| 2007/0005020 A1 | 1/2007 | Laveault |
| 2008/0249483 A1 | 10/2008 | Slenker et al. |
| 2009/0209916 A1 | 8/2009 | Peindl et al. |
| 2009/0270346 A1 | 10/2009 | Tijsma et al. |
| 2009/0291912 A1 | 11/2009 | Tijsma et al. |
| 2010/0298642 A1 | 11/2010 | Trusty et al. |

FOREIGN PATENT DOCUMENTS

| | | |
|---|---|---|
| EP | 2145599 A1 | 1/2010 |
| WO | 9619940 A1 | 7/1996 |
| WO | 9932185 A1 | 7/1999 |
| WO | 0071016 A1 | 11/2000 |
| WO | 0167961 A1 | 9/2001 |
| WO | 2004041424 A1 | 5/2004 |
| WO | 2005094665 A2 | 10/2005 |
| WO | 2008057802 A2 | 5/2008 |
| WO | 2009124407 A1 | 10/2009 |
| WO | 2010009563 A1 | 1/2010 |
| WO | 2010091527 A1 | 8/2010 |

* cited by examiner

MULTI-SECTIONED CANNULA WITH MULTIPLE LUMENS

TECHNICAL FIELD

This invention relates to a medical cannula used to deliver fluids.

BACKGROUND

Sinusitis is an inflammation of the mucosal tissue lining of the sinus walls which may lead to nasal passageway blockage, mucous stagnation and bacterial or fungal sinus cavity infection. Typical treatments begin with antibiotics. However, when antibiotics cannot relieve sinusitis, sinus surgery (which involves opening the sinus cavities and removing mucosal tissue) may be an alternative. Post-operative care for such surgery requires temporary and uncomfortable sinus packing or gauze which supports the reopened sinus passage and absorbs excess fluid while the tissues heal. After several days or at the discretion of the physician, the gauze packing is removed. Doing so is painful.

Sinus sealants and other biological materials have emerged as a promising technique to temporarily seal or otherwise protect the post-operative passageways with less intrusion and pain than that caused by traditional packing techniques.

SUMMARY OF THE INVENTION

Biomaterials have been used in ear, nose, and throat (ENT) procedures for surgical repair and drug delivery. The chemical nature of some biomaterials requires that they be provided in a multi-component form with the components being separated prior to use. The components are mixed together shortly before or during delivery, and the mixture rapidly forms a gel or solid.

There are, however, potential difficulties when using highly-reactive multi-component biomaterial systems. If the components react too rapidly, the resulting mixture may exhibit poor or erratic performance. Rapid reaction may however be desired for other reasons, such as a need for the biomaterial system to be spray-applied yet quickly form a gel or solid at a desired application site. An operator also desirably should be able to dispense the biomaterial using a single gloved hand.

Other concerns encountered using tissue sealants such as sinus sealants include navigating the sealant delivery system within a patient's anatomic structures. For example, sealants may be delivered through a cannula having one or more lumens through which fluids can flow. The cannula requires flexibility for insertion through various pathways that may twist and turn, sometimes abruptly at acute angles. At the same time, the cannula should be able to resist kinking or closing off of the lumen and permit uninterrupted fluid flow.

The invention provides, in one aspect, a multi-sectioned cannula comprising:
a) a malleable member having a proximal portion and a distal portion;
b) at least one lumen within and extending between the proximal and distal portion; the at least one lumen in fluid communication with a fluid supply; and;
c) a reinforcement member extending along the length of the at least one lumen; the cannula having a durometer such that the cannula does not kink when bent greater than 45 degrees.

The invention provides, in another aspect, a method of dispensing fluids to a target site, the method comprising:

A) providing a spray delivery system comprising:
  (i) at least one fluid supply; and
  (ii) a cannula, the cannula comprising:
    a) a malleable member having a proximal portion and a distal portion;
    b) at least one lumen within and extending between the proximal and distal portion; the at least one lumen in fluid communication with a fluid supply; and;
    c) a reinforcement member extending along the length of the at least one lumen; the cannula having a durometer such that the cannula does not kink when bent greater than 45 degrees; and
  (iii) a spray head through which the at least one fluid supply exits;
B) dispensing fluid from the fluid supply into the at least one such lumen and through the spray head.

The disclosed apparatus and method have particular use for accessing various anatomical locations such as sinus cavities and for applying tissue sealants at these anatomical locations.

BRIEF DESCRIPTION OF THE DRAWING

Like reference symbols in the various figures of the drawing indicate like elements. The elements in the drawing are not to scale.

DETAILED DESCRIPTION

The recitation of a numerical range using endpoints includes all numbers subsumed within that range (e.g., 1 to 5 includes 1, 1.5, 2, 2.75, 3, 3.80, 4, 5, etc.).

The present invention provides, in one aspect, a malleable, kink-resistant cannula and, in other aspects, a method of delivering tissue sealants using such cannula. The cannula can be bent to desirable configurations that are maintained during use and without the cannula or its lumen(s) kinking or closing off and thereby provide uninterrupted fluid delivery through the lumen(s). This kink-resistant feature permits the cannula to be shaped and reshaped during a sealant delivery process while fluid is flowing through the cannula.

The cannula may be assembled to a delivery system and spray head that may be used to apply multi-component fluid compositions. Such delivery systems and spray heads, for example, include those described in U.S. patent application Ser. No. 13/284,600 and U.S. patent application Ser. No. 13/284,421, respectively, filed even date herewith and each of which is incorporated herein by reference in its entirety.

The apparatus and method may be used to apply compositions containing multiple agents, such as a multiple component tissue sealant (e.g. two components) to a variety of bodily passageways or cavities including nasal cavities and sinus cavities (e.g. maxillary, frontal or sphenoid sinuses).

Exemplary multi-component tissue sealants may include reactive polysaccharides, for example, chitosan and starch. Other exemplary multi-component tissue sealants are provided in U.S. patent application Ser. No. 12/429,141, now published as U.S. Patent Application Publication No. 2009/0270346A1 and U.S. patent application Ser. No. 12/429,150, now published as U.S. Patent Application Publication No. 2009/0291912 A1.

Figure 1:
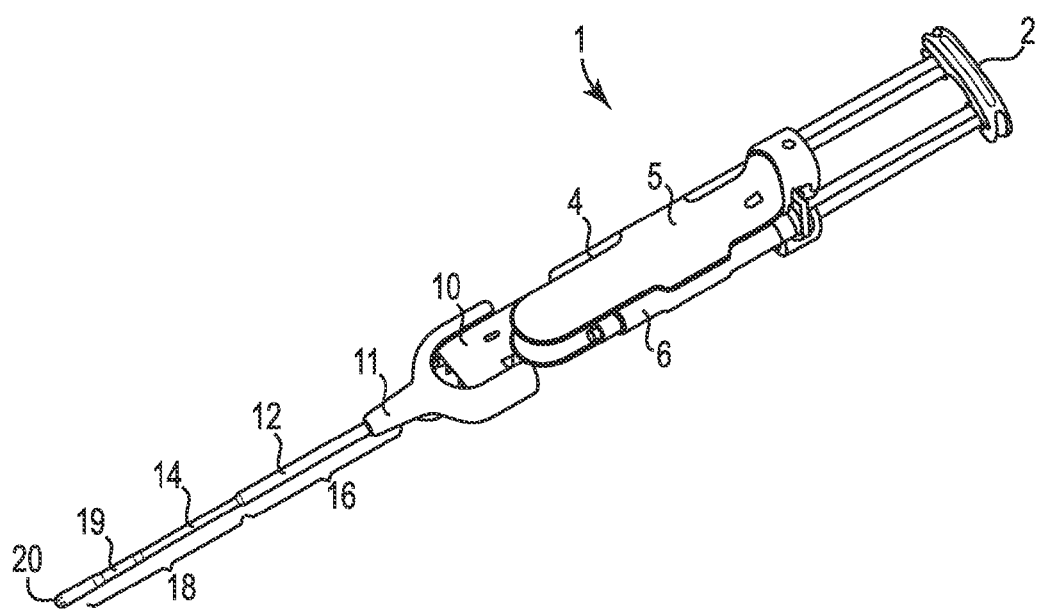
FIG. 1 is a perspective view of a partially assembled spray delivery system including an exemplary cannula.

FIG. 1, which shows a partially assembled spray delivery system 1, includes an actuating member 2, and a body 5 capable of receiving and capturing syringes 4, 6. The actuating member 2 operates upon syringes 4, 6 to provide simultaneous delivery of fluids housed in syringes 4, 6. The spray delivery system 1, as shown in FIG. 1, further includes cannula 14 and spray head 20.

Cannula 14 may be a flexible or malleable member that may be assembled to include a rigid proximal end portion 16 and a malleable distal end portion 18. The rigid proximal end portion 16 may be constrained at the proximal end by support shaft 12 and shroud 11, which prevents or discourages cannula bending. The rigid proximal end portion 16 also includes the portion of cannula 14 surrounded by support shaft 12. Cannula 14 may be bent at the malleable distal end portion 18, which extends from the end of the support shaft 12 up to the proximal portion of the spray head 20.

Cannula 14 and spray head 20 are connected to body 5 through manifold 10. Manifold 10 may be surrounded by a shroud 11 with support shaft 12 constraining the proximal end of cannula 14. Manifold 10 may be configured to receive portions of syringes 4, 6 without requiring threaded or rotating engagement of the syringe to manifold 10 to provide a liquid tight connection. Spray head 20 is connected to malleable distal end portion 18. Covering the interface between the malleable distal end portion 18 and spray head 20 is a sheath 19 which provides a smooth transitional interface at the joint between cannula 14 and spray head 20.

When used to deliver a tissue sealant to a sinus cavity, cannula 14 preferably has an overall length of about 10 cm to 15 cm, more preferably about 12 to 13 cm. The rigid proximal end portion 16 may have a length in the range from about 4 cm to 8 cm, preferably about 5 cm to 7 cm, and the malleable distal end portion 18 may have a length, for example, in the range from about 4 cm to 8 cm, preferably about 5 cm to 7 cm. The outer diameter of cannula 14 may be from about 0.1 cm to 1.0 cm, preferably about 0.3 cm to 0.4 cm. The ratio of the rigid proximal end portion 16 to the malleable distal end portion 18 may be in a ratio of about 2:1 or about 1:2, and preferably about 1:1.

Depending on the specific cannula use, other dimensions are also acceptable. For example, cannula 14 may be used in laparoscopic anatomical or gynecological surgery, neural surgery, pulmonary surgery or the like.

The cannula 14 may be formed of a material acceptable for use inside the human body and of a selected durometer (hardness). The selected durometer aids in preventing the cannula from kinking when bent greater than 45 degrees, greater than 90 degrees, or greater than 180 degrees with respect to a straight, unbent configuration. The selected material may include for example, thermoplastic or thermoset polymers such as polyolefins, silicones, polyvinyl chlorides, polyurethanes, polyesters and the like. To attain a desired durometer, fillers or plasticizers may be used. The amount and type of filler or plasticizer is determined by the selected thermoplastic or thermoset polymers used. Cannula 14 may have a durometer (Shore A) in the range, for example, from 60 to 95, preferably from about 85 to 95.

Figure 2:
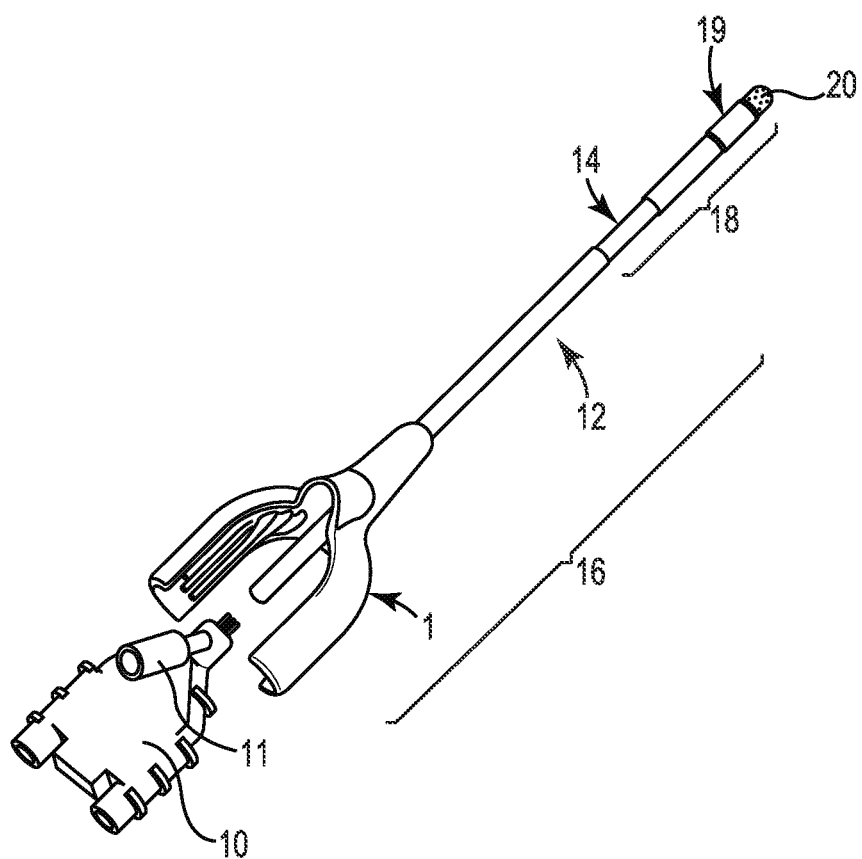
FIG. 2 is a perspective, exploded view of the cannula of FIG. 1.

Referring to FIG. 2, support member 12 may be in the form of a cylindrical metal or plastic tube surrounding cannula 14 and molded within or otherwise connected to the distal end portion of shroud 11, for example, by adhesive or welding. The support member 12 preferably is made of stainless steel. Other exemplary materials include, for example, metals such aluminum and plastics such as thermoplastic or thermoset polymers. The support member 12 desirably has a thickness and length such that it minimizes physical obstruction during anatomic insertion and resists sideways deflection of proximal end portion 16 so as to provide improved control when maneuvering and navigating cannula 14 through bodily passageways. The support member 12 may, for example, have a thickness of about 0.01 cm to about 0.1 cm, preferably from about 0.02 cm to 0.03 cm; and a length, for example, of about 3 cm to 10 cm, preferably from about 4.5 cm to 5.5 cm.

Figure 3A:
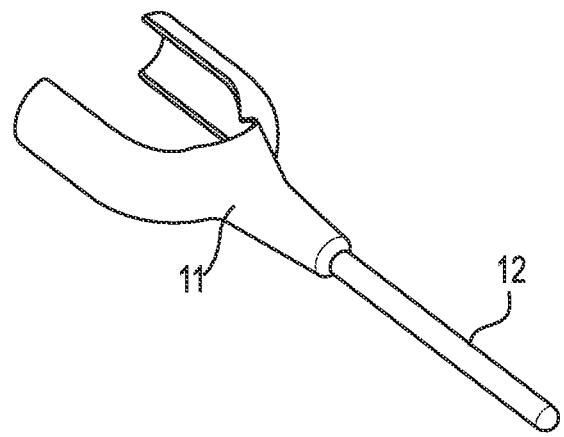
FIG. 3A is a perspective view of a shroud and support member.
Figure 3B:
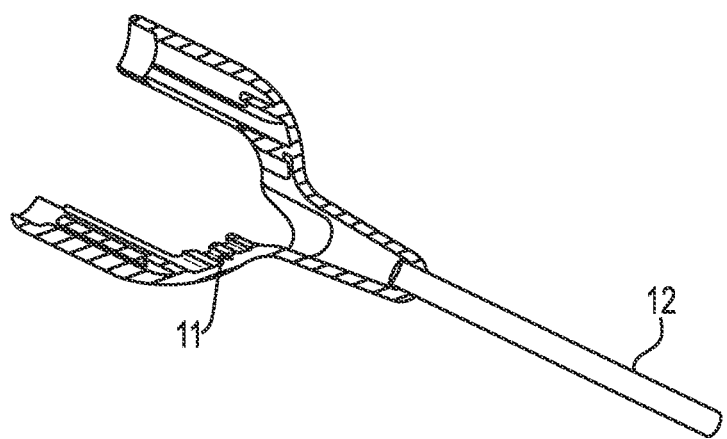
FIG. 3B is a perspective view, partially in cross-section of the FIG. 3A shroud.

As illustrated in FIGS. 2 and 3A-B, shroud or casing 11 surrounds outer portions of manifold 10. The shroud 11 also engages the support member 12, and when assembled to cannula 14, provides additional proximal rigidity to the cannula 14. Shroud 11 may be permanently attached to the manifold 10, for example, by adhesives, welding or injection molding or may be optionally removable.

Figure 4A:
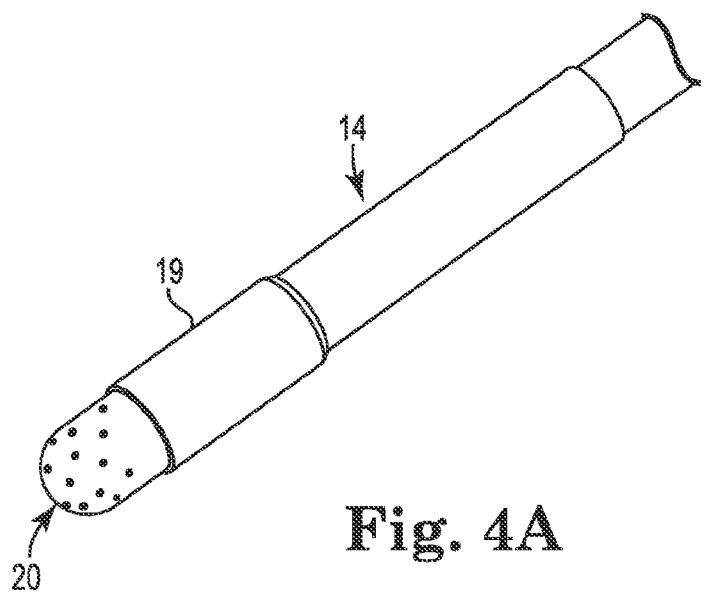
FIG. 4A is a perspective view of a distal portion of the cannula.
Figure 4B:
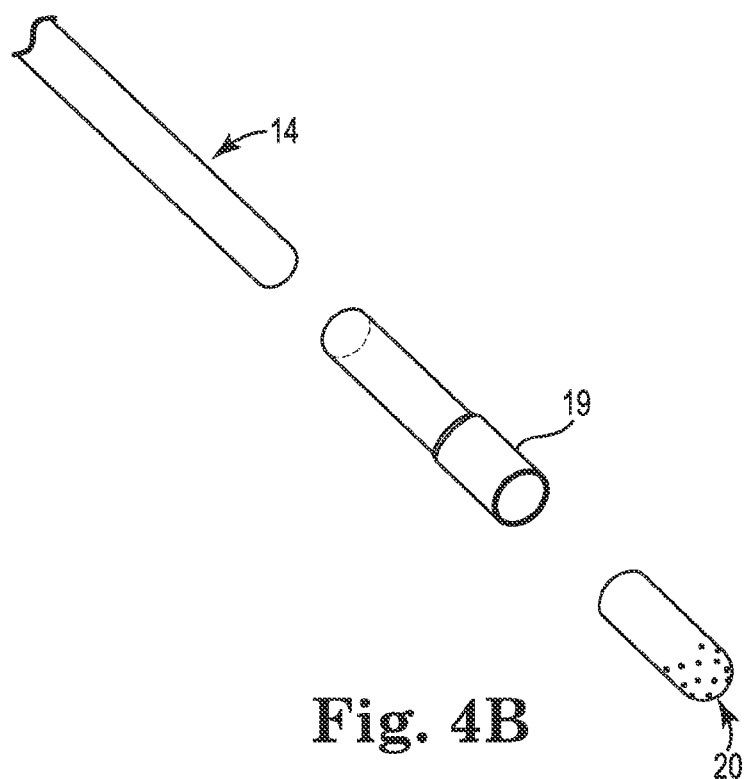
FIG. 4B is a perspective, exploded view of components in the FIG. 4A cannula.

As illustrated in FIGS. 4A-B, sheath 19 may, for example, surround the proximal portion of spray head 20 and the distal end portion 18 producing a smooth interface between the spray head 20 and cannula 14. Sheath 19 also helps keep spray head 20 firmly attached to cannula 14 when withdrawing spray head 20 from a confined location.

Desirable lengths of sheath 19 may for example, range from about 10 mm to 50 mm, preferably from about 20 mm to 25 mm. A thickness for sheath 19 desirably may be selected such that it minimizes interference with anatomical features during cannula insertion. The sheath thickness may, for example, range from to 0.001 cm to 0.010 cm, preferably 0.001 cm to 0.003 cm. The sheath 19 may be a heat shrink tube, a mechanically expanded tube, or an extruded plastic tube, and may be made from a variety of materials, for example, polyester, polyolefin, and fluoropolymers.

Figure 5A:
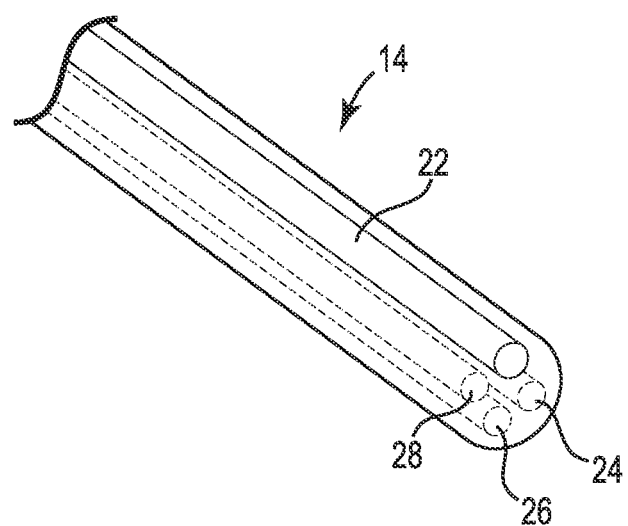
FIGS. 5A-B are perspective views, partially in phantom, of the FIGS. 4A and 4B cannula.
Figure 5B:
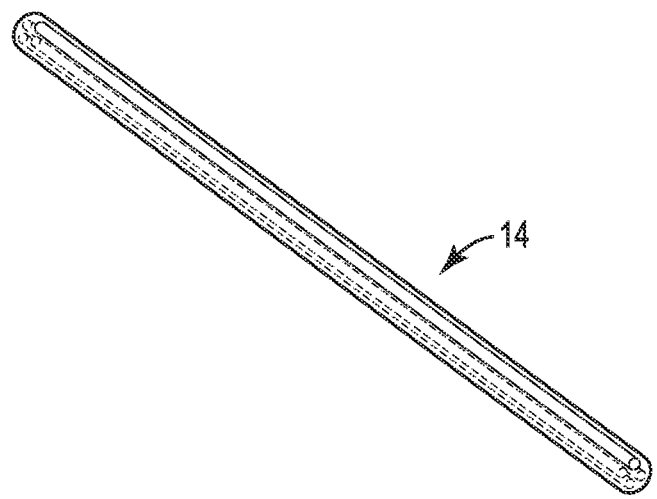

As shown in FIGS. 5A-B, an exemplary cannula 14 may enclose multiple lumens that extend the entire cannula length, from the rigid proximal end portion 16 to the malleable distal end portion 18 and maintains the separation of each lumen. The individual lumen diameters are dependent on a number of factors, including the spray head opening diameters, the desired pressure and flow rate. The lumens may, for example, all be of the same diameter and cross sectional shape. The lumen shape may be, for example, circular, oval, square or D-shaped in cross-section, with the flat portions of neighboring D-shapes being adjacent to one another.

As illustrated in FIG. 5A, at least one of the lumens may include a reinforcement member 22 to allow selective bending of the cannula 14 to fit different orientations. The reinforcement member 22 may, for example, be in the form of a wire located within and extending along the length of a lumen. The reinforcement member 22 may, but need not be centrally located in the multi-lumen cannula 14. In such embodiments, the cannula 14 may be formed with at least two lumens, one of which will become occupied by the reinforcement member 22. The cannula 14 may also be formed by extruding or molding it over the reinforcement member 22 and by providing at least one lumen through which fluid may flow.

The reinforcement member 22 may be made of, for example, metal or a metal alloy such as stainless steel, copper, aluminum or the like. In other examples, reinforcement member 22 may be made of a shape memory metal such as Nitinol.

The diameter of the reinforcement member 22, may, for example, range from 0.001 cm to 0.10 cm, preferably 0.03 cm to 0.05 cm. The shape of the reinforcement member 22 may be, for example, circular, oval, square or D-shaped in cross-section. The stiffness of the reinforcement member 22 may be full hard, half hard, quarter hard, annealed, soft or any other desired stiffness depending on the desired application.

The cannula 14, illustrated in FIGS. 5A-B, includes four lumens, one of which is occupied by reinforcement member 22. Remaining lumens 24, 26, 28 are in fluid communication with one or more fluid supplies such as syringes 4, 6 and a source of pressurized air (not shown) that may be introduced into lumen 28 via port 30, which is shown in FIG. 2.

In one exemplary assembly process for the disclosed device, an operator first inserts the actuating member 2 into body 5. Alternatively, actuating member 2 may be preassembled with body 5. Syringes 4, 6 are positioned against body 5 and actuating member 2 so that body 5 and actuating member 2 can receive and capture syringes 4, 6. In this manner, syringes 4, 6 are held substantially parallel in body 5.

Once the syringes are received and captured by body 5, cannula 14 and spray head 20 are assembled to body 5 through manifold 10. Cannula 14 and spray head 20 may if desired be preassembled to manifold 10 during manufacturing.

The operator then connects manifold 10 to syringe outlets to provide an unthreaded, liquid-tight connection such that the syringe contents in syringe barrels are in fluid communication with cannula 14 through manifold 10.

When the delivery device 1 is fully assembled, the operator shapes the cannula 14 to a desired shape. Cannula 14 desirably is sufficiently stiff so that it will retain its shape until bent into a new shape. The shaped cannula 14 and spray head 20 are then maneuvered or navigated into a desired treatment site within the patient's body, for example, a nasal or sinus cavity or other opening, recess or passageway. Once satisfactorily positioned, an operator may, for example, depress actuating member 2 to move the plunger of syringe 4, 6 toward the syringe outlets, advancing the fluid syringe contents substantially at the same time through the separate syringe barrels and out into respective fluid channels in manifold 10 which maintain the fluid separation. Continued force will advance the fluids through the multi-lumen cannula 14 and into a region within spray head 20 where they mix before the mixed fluids exit spray head 20. If compressed gas is used, it may be supplied through a gas inlet (not shown). The gas stream passes through a lumen of multi-lumen cannula 14 into the mixing region of spray head 20. The gas stream helps atomize the mixed syringe contents resulting in much smaller droplets. Overall, a smoother manipulation and easier control of the device through passageways is provided.

The invention is further illustrated in the following non-limiting examples.

Example 1

Delivery device 1 was clamped into a suitable fixture and evaluated using an air flow rate meter to determine rate of air flow through cannula 14 at different user configurations. The air flow rate was measured at least 14 times for each user configuration.

| Test | Average Air Flow Rate (L/min) | STDEV |
| --- | --- | --- |
| Air Flow Rate (Straight Cannula) | 10.02 | 0.47 |
| Air Flow Rate (90° Bent Cannula) | 10.05 | 0.43 |
| Air Flow Rate (180° Bent cannula) | 10.29 | 0.88 |
| Air Flow Rate (Greater than 180° Bent Cannula | 9.89 | 0.30 |

Example 2

Delivery device 1 was clamped into a suitable fixture and evaluated using a calibrated force gauge to determine the force in Lbf units to bend the cannula 90 degrees. The required force was measured at least 14 times with the cannula bent at 90 degrees.

| Test | Average (Lbf) | STDEV |
| --- | --- | --- |
| Cannula Bend Force (90°) | 1.53 | 0.11 |

We claim:

1. A cannula comprising:
   a) a rigid proximal portion connected to a malleable distal portion;
   b) a first polymeric lumen and at least a second polymeric lumen within and extending between the rigid proximal portion and malleable distal portion;
   c) the first polymeric lumen having a malleable reinforcement member within and extending along the length of the malleable distal portion; and
   d) the at least second polymeric lumen being in fluid communication with a fluid supply;
   wherein the connected malleable distal portion and rigid proximal portion can be inserted and maneuvered into a human nasal cavity, the rigid proximal portion prevents or discourages cannula bending if maneuvering in such cavity, the malleable distal portion has a durometer such that the malleable distal portion does not kink when bent greater than 45 degrees, and the malleable reinforcement member is sufficiently stiff so that the malleable distal portion will retain its shape until bent into a new shape.

2. The cannula of claim 1 wherein the malleable distal portion does not kink when bent 90 degrees.

3. The cannula of claim 1 wherein the malleable distal portion does not kink when bent 180 degrees.

4. The cannula of claim 1 wherein the malleable distal portion durometer is about 60-95 Shore A.

5. The cannula of claim 1 wherein the malleable distal portion comprises polyvinyl chloride.

6. The cannula of claim 1 wherein the rigid proximal portion includes a rigid support member comprising a cylindrical metal or plastic tube.

7. The cannula of claim 6 wherein the support member comprises stainless steel.

8. The cannula of claim 1 wherein the malleable distal portion is connected to a spray head.

9. The cannula of claim 8 further comprising a sheath that provides a smooth transitional interface between the cannula and spray head.

10. The cannula of claim 9 wherein the sheath comprises polyester.

11. The cannula of claim 1 wherein the cannula is dimensioned for use in a sinus cavity, the rigid proximal portion and the malleable distal portion each have a length, and the rigid proximal portion length and the malleable distal portion length are in a ratio of about 1:2 to about 2:1.

12. The cannula of claim 1 wherein the cannula includes four lumens.

13. The cannula of claim 1 wherein the cannula includes at least two lumens configured to be in fluid communication with separate fluid supplies.

14. The cannula of claim 1 wherein the reinforcement member comprises a stainless steel wire.

15. The cannula of claim 11 wherein the rigid proximal portion and malleable distal portion have an overall length of about 10 cm to 15 cm.

16. The cannula of claim 11 wherein the rigid proximal portion has a length of about 3 cm to 10 cm, the malleable end portion has a length of about 4 cm to 8 cm and the cannula has an outer diameter of about 0.1 cm to 1.0 cm.

17. The cannula of claim 1 wherein the rigid proximal portion and malleable distal portion have an overall length of about 10 cm to 15 cm and an outer diameter of about 0.3 to 0.4 cm.

18. The cannula of claim 1 further comprising a manifold configured to receive at least two syringes in fluid communication with a lumen in the cannula.

19. The cannula of claim 18 further comprising a shroud surrounding the manifold and providing additional proximal rigidity to the cannula.

20. The cannula of claim 1 wherein the cannula is dimensioned for use in a laparoscopic surgery site.

21. The cannula of claim 1 wherein the cannula is dimensioned for use in a neural surgery site.

22. The cannula of claim 1 wherein the cannula is dimensioned for use in a pulmonary surgery site.

23. A method of dispensing fluids to a body cavity target site, the method comprising:
  A) providing a spray delivery system comprising:
    (i) at least one fluid supply; and
    (ii) a cannula, the cannula comprising:
      a) a rigid proximal portion connected to a malleable distal portion;
      b) a first polymeric lumen and at least a second polymeric lumen within and extending between the rigid proximal portion and malleable distal portion;
      c) the first polymeric lumen having a malleable reinforcement member within and extending along the length of the malleable distal portion; and
      d) the at least second polymeric lumen being in fluid communication with a fluid supply;
    wherein the connected malleable distal portion and rigid proximal portion can be inserted and maneuvered into a human nasal cavity, the rigid proximal portion prevents or discourages cannula bending if maneuvering in such cavity, the malleable distal portion has a durometer such that the cannula does not kink when bent greater than 45 degrees, and the malleable reinforcement member is sufficiently stiff so that the malleable distal portion will retain its shape until bent into a new shape; and
    (iii) a spray head through which the at least one fluid supply exits; and
  B) dispensing fluid from the fluid supply into the at least second polymeric lumen and through the spray head.

24. The method of claim 23 wherein the malleable distal portion has a durometer (Shore A) from 60-95.

25. The method of claim 23 wherein the malleable distal portion does not kink when bent 90 degrees.

26. The method of claim 23 wherein the malleable distal portion does not kink when bent 180 degrees.

27. The method of claim 23 comprising dispensing a tissue sealant.

28. The method of claim 23 comprising dispensing a mixture of chitosan and starch.

\* \* \* \* \*